(12) United States Patent
Nguyen

(10) Patent No.: US 8,409,558 B2
(45) Date of Patent: Apr. 2, 2013

(54) METHOD FOR TREATMENT OF ONYCHOMYCOSIS

(76) Inventor: Tim The Nguyen, Oxnard, CA (US)

(*) Notice: Subject to any disclaimer, the term of this patent is extended or adjusted under 35 U.S.C. 154(b) by 1037 days.

(21) Appl. No.: 11/836,300

(22) Filed: Aug. 9, 2007

(65) Prior Publication Data

US 2007/0274935 A1    Nov. 29, 2007

Related U.S. Application Data

(63) Continuation-in-part of application No. PCT/US2006/006767, filed on Feb. 22, 2006.

(60) Provisional application No. 60/593,895, filed on Feb. 22, 2005.

(51) Int. Cl.
*A61K 31/74* (2006.01)

(52) U.S. Cl. .................................... 424/78.08

(58) Field of Classification Search ................ None
See application file for complete search history.

(56) References Cited

U.S. PATENT DOCUMENTS

| | | | |
|---|---|---|---|
| 4,180,058 A * | 12/1979 | Brem | 128/898 |
| 6,001,345 A | 12/1999 | Askill et al. | |
| 6,207,193 B1 | 3/2001 | Pellegrini | |
| 6,250,311 B1 | 6/2001 | Megna | |
| 6,455,033 B1 | 9/2002 | Steffier | |
| 6,746,667 B2 | 6/2004 | Badejo et al. | |
| 6,756,051 B1 | 6/2004 | Chen | |
| 6,919,076 B1 | 7/2005 | Green | |
| 6,942,875 B2 * | 9/2005 | Hedgpeth | 424/448 |
| 7,056,533 B2 | 6/2006 | Chudzik | |
| 2001/0046478 A1 | 11/2001 | Bohn et al. | |
| 2004/0137067 A1 | 7/2004 | Narang | |
| 2004/0151688 A1 | 8/2004 | Sherbondy | |
| 2004/0175353 A1 * | 9/2004 | Lyster | 424/78.35 |
| 2005/0191337 A1 | 9/2005 | Gueret | |
| 2005/0271694 A1 | 12/2005 | Mansouri et al. | |
| 2006/0073219 A1 * | 4/2006 | Selner | 424/739 |
| 2006/0115440 A1 | 6/2006 | Arata | |

OTHER PUBLICATIONS http://www.ehow.com/list_6814391_pediatric-dentistry-instruments.html, accessed Sep. 17, 2011.*

Narang Upvan, Mainwaring Lawrence, Spath Gina; In-vitro analysis for microbial barrier properties of 2-octyl cyanoacrylate-derived wound treatment films, Journal of cutaneous medicine and surgery, vol. 7, No. 1, Jan.-Feb. 2003, p. 13-9, United States.

* cited by examiner

*Primary Examiner* — Paul Dickinson
(74) *Attorney, Agent, or Firm* — Ralph D. Chabot

(57) ABSTRACT

Onychomycosis present in a nail is treated by debridement such as grinding a portion of the nail, which includes an infected portion and thereafter applying a composition containing alkyl cyanoacrylate to the debrided surface which cures to a hard layer. The hard layer can be successively ground and coated with successive layers of alkyl cycanoacrylate.

5 Claims, No Drawings

METHOD FOR TREATMENT OF ONYCHOMYCOSIS

CROSS-REFERENCE TO RELATED APPLICATION

This application claims priority to PCT Application No. PCT/US2006/006767 filed Feb. 22, 2006 which claims priority to U.S. Provisional Application No. 60/593,895, filed Feb. 22, 2005.

TECHNICAL FIELD

This disclosure relates to treatment of nail fungi and, more particularly, to a novel, effective topical treatment of toenail and fingernail fungi.

BACKGROUND OF THE INVENTION

Fungi includes yeasts, molds, rusts and mushrooms. Of the 100,000 known species, only 150 regularly cause disease. Dermatophytes which include tinea ungium are the main cause of onychomycosis the detachment of the nail from its bed at its distal or lateral attachments especially in the dark, sweaty environment of nails. The fungi usually create damage to the nail in the form of micropores. They also cause unsightly discoloration and thickening of the nails and attack the tissue in the nail bed under the nails. Continued presence of the fungi can lead to secondary bacterial infection of the toes or fingers.

20% of the U.S. population between ages 40 and 60 have nail fungus. There are 70 million who have nail and/or skin disease caused by fungi. In 2004, $17.4 billion dollars was spent in the United States for relief. Topical antifungals used for treatment of nail fungal disease are not nearly as effective against tinea capitis and tinea corporis. The following older topical treatments are still available over the counter (OTC).

The old, but still available
Whitfield's ointment
Tolnaftate
Undecylenic acid
Topical amphotercian B
Haloprogin
Castellani's Paint
Cyclopirox The following modern OTC topicals are also available. None of these topical treatments provide permanent treatment of nail fungus.

The Modern newer topicals
Azoles (ketoconazole, econazole, et al.)
Polyene antibiotics (nystatin, natamycin)
Allyamines (naftifine HCl, terbinafine)
Hydroxypyridones (ciclopirox)
Morpholines (amorolfine)

Systematic antifungals such as griseofulvin, amphotericin B, imidazoles, triazoles, flucytosine or terbinafine must be taken for several months while closely monitoring liver enzymes since there is risk of damage to the liver.

The selling price of typical nail fungus medicines is as follows:

| Medication | Amount | Cost |
| --- | --- | --- |
| Lamasil (terbinafine) | 90 tablets | $971.66 |
| Sporanox (traconazole) | 84 tablets | $797.71 |
| Penlac (cyclopiox 8% laquer) | 6.6 ml | $147.00 |

E. M. Warshaw et al. in a double blind study reported (October 2005, American Academy of Dermatology) that continuous ingestion of Lamisil was far superior to pulse therapy and that continuous therapy only provided 71% mycological cure and 41% complete cure. Cure of all nails only occurred in 25% of the subjects.

Nail lacquers may induce side effects such as sensitization and allergic contact dermatitis (European Journal of Dermatology, Volume 10, Number 3, 223-5, Avril-Mai 2000. In a case study, it was found that after preformed acrylic nails bonded with Ethylcyanoacrylate (ECA) were removed after 3 weeks, oncychomycosis was revealed.

STATEMENT OF THE INVENTION

It has surprisingly been discovered that selectively applying a topical coating of alkyl cyanoacrylate such as cyanoacrylate esters or cyanoacrylate ethyl to a substantially debrided area of the diseased nail results in an effective elimination of the fungus growth. In a preferred embodiment, periodic debridement such as grinding is performed and thereafter reapplication of the topical coatings. This procedure promotes return of the nail to a healthy condition.

In this disclosure, the term "comprising" means including the elements or steps that are identified following that term, but any such elements or steps are not exhaustive, and an embodiment may include other elements or steps.

It is realized that other formulations exist which contain cyanoacrylate. However, to the extent these other formulations exist, they do not describe that the chemicals contained therein as effectively promoting the treatment of onychomycosis.

Fungal growth requires air, a substrate such as keratin of the nail, and water or moisture such as from hot sweaty feet. However, alkyl cyanoacrylates such as $c_1$ to $c_{10}$ cyanoacrylate esters or cyanoacrylate ethyl bind to keratin to form a hard film encapsulating the fungus and yeast that grow within keratin. This prevents further growth of the yeast and fungus.

The hard film that forms is impervious to moisture and air which eliminates necessary ingredients for fungus and yeast growth. Periodic debridement of the bonded composition which includes encapsulated fungus is necessary to facilitate subsequent absorbing of a portion of the solution to eventually, over time, achieve complete removal of the fungus from the initially infected region of a nail.

Liquid compositions containing alkyl cyanoacrylate such as cyanoacrylate ester or cyanoacrylate ethyl have chemical properties capable of effectively controlling fungal nail disease. Although cyanoacrylate itself is capable of controlling fungi and yeast growth, the additional use of an effective amount of anti-fungal agents will have the advantageous effect of significantly enhancing this controlling effect. When such a liquid is applied to the surface of a toenail or fingernail infected with onychomycosis, it can penetrate beneath the nail surface into the micro pores created by fungi and fill in these voids. After the liquid has been applied to the nail (about 3 to 5 minutes), the liquid solidifies and forms a moisture and air barrier. Nails treated with a cyanoacrylate liquid will harden. The region formed by the nail/hardened plastic combination is sufficiently durable to maintain its condition for up to two weeks. The hardened plastic effectively forms a moisture and air barrier. Without moisture or air, onychomycosis is incapable of further nail degradation and the disease can effectively be controlled or even eliminated. The cured composition also helps to cosmetically enhance the nail surface as the unsightly nail surface infected with onychomycosis has been solidified or unified into a uniform or smooth exterior surface.

Accordingly, my disclosure describes a method for treating a nail infected with onychomycosis by application of an effective amount of a liquid composition containing a cyanoacrylate ester or cyanoacrylate ethyl (alkyl cyanoacrylate) to form a substantially impermeable barrier to prevent further supply of moisture and air to the fungus necessary for continued growth. My method includes periodic debridement of the infected nail surface, thus removing not only a portion of the infected nail but also a portion of the previous application of the cured cyanoacrylate composition. Accordingly, immediately following debridement, a subsequent application of an effective amount of the liquid composition is necessary to create a replacement moisture/air barrier.

Additionally, and as will be described in more detail later, it has been found that a synergistic effect occurs when alkyl cyanoacrylate such as cyanoacrylate ester or ethyl is combined with an effective amount of an antifungal agent. The synergistic effect achieves complete elimination of the fungus faster than if the cyanoacrylate or antifungal agent were used separately.

Alkyl cyanoacrylate such as cyanoacrylate esters or cyanoacrylate ethyl have high absorbing ability; they are good vehicles for delivery of other antifungal medications such as Clotrimazole, Nystatin Griseofulvin, Ketoconazole, Terbinafine, Itraconazole and others. Therefore, mixing an alkyl cyanoacrylate derivative with one of the antifungal medications may have an enhanced treatment effect on onychomycotic fungi. Addition of 0.1 to 10% and preferably 0.5-2% of an anti-fungal agent such as undecylenic acid has been shown to inhibit the spread of infection and to remove the yellow-color of infected nails.

The fungus infected nail becomes porous. The viscosity of the coating solution is selected such that the solution enters the pores and progresses through the thickness of the nail to the nail bed.

A composition containing a popular cyanoacrylate is SUPERGLUE. The adhesive characteristic is provided by methyl cyanoacrylate.

The alkyl cyanoacrylate derivatives have the general formula:

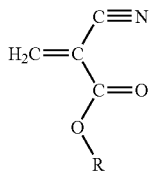

Where R is the alkyl group which has 1 to 12 carbon atoms. It is to be understood that alkyl groups may be developed in the future which may include more than 12 carbon atoms and such newly developed compositions should considered as being covered by my invention.

The preferred cyanoacrylate is ethylcyanoacrylate (ECA) though there are many other commercially available esters where R is propyl, butyl, octyl, or their mixtures, are available and will form impervious, films.

Contrary to popular understanding, cyanoacrylate does not air dry. In fact, cyanoacrylates cure (convert from liquid to solid) in the presense of weak bases such as water, alcohol, and blood. At normal conditions, a thin layer of water is present on almost all surfaces. This accounts for many unintended adhesions involving appendages and/or expensive tools. The curing process involves the anionic chain polymerization reaction, which occurs as follows: In the chain-initiating step, the weak base (X) donates an electron pair to a cyanoacrylate monomer. The $CH_2$ group is highly electropositive as a result of the electron-withdrawing properties of the cyanide and ester groups; therefore, the electron pair is attracted to this region. The attraction alters the carbon-carbon double bond to create bonding sites of both ends of the reactant group.

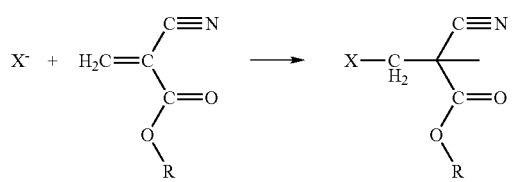

In this manner, the electron pair is passed on in chain propagation as each monomer alters the next. Bonds form between monomers, ultimately creating the powerfully adhesive polymer changes of cured cyanoacrylate glue.

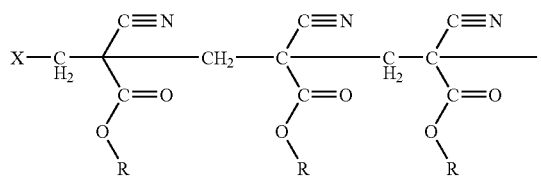

| FORMULA 2-ETHYL CYANO ACRYLATE OR (2-ETHYLCYANO 2-PROPENOATE) | |
|---|---|

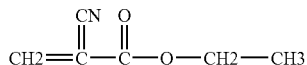

| PROPERTIES | |
|---|---|
| Liquid State | Super Glue |
| Chemical Base | Ethyl Cyanoacrylate |
| Viscosity, cps | 30-70 |
| Color | Colorless Liquid |
| Vapor Pressure (@ 70° C., mmHg) | 10 |
| Specific Gravity (25° F./4° C.) | 1.06 |
| Flashpoint TCC ° F. (° C.) | 185 (85) |
| Soluble In: | Acetone, MEK, Nitromethane |
| Cured State | Super Glue |
| Softening Point | 306° F. (153° C.) |
| Melting Point | 365° F. (185° C.) |
| Temperature Range | −65° F. to +180° F. (−54° C. to +82° C.) |
| Rockwell Hardness (M) | 74 |
| Typical Gap (Inches) | .004 |
| Soluble In: | Pacer X-8 Debonder, Acetone, Nitromethane |
| Tensile Strength, steel, ASTM-D2095 | 4700 psi |
| Impact Strength, steel, ASTM-950 | 7-10 ft-lbs |
| Tensile Shear Strength, ASTM-D1002 (psi) | |
| Steel | 2500 |
| Aluminum | 1600 |
| ABS | 665* |
| Nylon | 850* |

-continued

FORMULA 2-ETHYL CYANO ACRYLATE
OR (2-ETHYLCYANO 2-PROPENOATE)

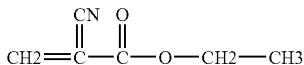

PROPERTIES

| Rigid PVC | 700* |
| --- | --- |
| SBR | 85* |
| EPDM | 100 |

*substrate failure

The synergistic effect achieved combining cyanoacrylate with an antifungal agent results in a more powerful fungicidal compound. As the mixture is applied over the infected nails, a portion is absorbed into the micro pores of the damaged nail and then dries quickly (i.e. in seconds) to change the infected/damaged area applied with the compound to an air and moisture impervious region containing antifungal agent. The fungi are trapped in this region with no further source of air or moisture. The damaged nail within this region which used to be the food source of fungi now has been substantially encapsulated by the compound.

During the process of biodegradation of the infected nail, the antifungal agent will come in contact with the infected area and kill the fungus. Cyanoacrylate forms very strong bonds with the keratin present in the nails, unlike lacquer which is primarily a paint applied on the surface of the nail and has minimal penetration/absorption quality.

When applied properly, the bond formed by the interaction of my formula with a severely infected nail may last up to 2 weeks. However, a nail mildly or slightly infected may last longer and upwards to two months. This bond forms an impervious layer of cyanoacrylate to block the absorption of air and water by the fungus trapped within the bonded region. This interference with the food chain for the fungus substantially reduces and eventually eliminates its growth.

In my preferred embodiment, weekly debridement of the damaged nail is an essential part of the treatment. Following debridement, my cyanoacrylate/antifungal compound is reapplied.

Application and Cure Characteristics:

For best results, use an effective amount of liquid composition. In general, one free falling drop covers one square inch of nail area having a thickness of approximately 0.002". The cure rate of the liquid composition is dependent upon temperature, relative humidity, thickness, and surfaces being bonded.

Alkyl cyanoacrylate adhesives are actually a solution of prepolymers of the ester in the ester monomer. Viscosity is adjusted by the degree of polymerization of the ester. Preferred viscosity of an ECA is 5 cP to 100 cP which will fill micropores from 0.002" to 0.005". Cure rate is affected by the amount of a stabilizer such as 100-2000 ppm of hydroquinone or other suitable stabilizer. The monomer can also act as a solvent for other antifungals, such as 0.1 to 10% and preferably 0.5 to 5% of an anti-fungal agent such as undecylenic acid. An additional film forms such as below 10% by weight, suitably 1 to 9% of a compatible acrylic polymer which dissolves in the cynoacrylate monomer such as polymethylmethacrylate may also be present.

To obtain the most effective treatment, the nail area infected with onychomycosis fungi should be removed to the extent reasonably possible preferably by first mechanically grinding away the infected nail down to the level of the normal nail, and then secondly applying a small amount of the composition. Care should be taken to make certain the composition covers the infected area and also that sufficient amounts are used to saturate as well and to produce a thin coating on the infected area of nail. Applications can be with or without a brush, while not accidentally spilling onto the skin. Application of cyanoacrylate to the skin between the toes can undesirably cause a bonding to the skin in a matter of seconds and may be difficult to remove.

Grinding and recoating can be repeated from at least every 3 days to 6 weeks, and preferably, every one to three weeks for a total of two to six months or until a new nail is fully grown. The coating usually starts to lift at edges after 1 week. Further treatment can be assigned to the patient to do further debridment with an emery board or other tool at home and using a drop or brush application for the composition. Although hard cyanoacrylate is preferred for nail polish to be applied over the cured layer of cyanoacrylate, softer cyanoacrylate, similar to a liquid bandage may be used for easier debridement.

The following composition for the treatment of onychomycosis was prepared:

|  | Weight Percent |
| --- | --- |
| Ethyl cyanoacrylate | 90.5 |
| Hydroquinone | 0.4 |
| Undecylenic acid | 0.1 |
| Polymethylmethacrylate | 9.0 |

Methods 154 patients between the ages of 10 years and 100 years were enrolled by a podiatrist and a dermatologist.

1. Duration of Nail Disease: months to decades (onset World War II, Korean War, Vietnam War, etc.)

2. Secondary Diseases: diabetes, peripheral vascular disease, post trauma infection to the nail and surrounding area and obesity.

3. Pretreatment Diagnosis: clinical, KOH, PAS-D of nail clippings and cultures on Sabourads agar.

4. Clinical Improvement Assessed With: a) patient satisfaction, b) color, c) thickness and d) new unaffected nail growth.

5. Initial Visit: cultures, photos, debridement with Dremel® sanding tool and then application of topical test material. This was repeated at 1 or 2 week intervals dependent upon severity of nail disease for the $2^{nd}$ and $3^{rd}$ visits.

6. Subsequent Visits: At 1 or 2 month intervals dependent upon patient's ability to home treat with emery (sandpaper) boards and home application brush tipped tubes of medication.

Results

1. In an initial clinical evaluation:
Patient Satisfaction 85%-95% at 1-2 months
Color Improvement 80%-90% at 2-3 months
Reduced Thickness 92%-95% at 2-4 months 2. Toenail Culture Data: See results below In a clinical trial, 154 patients were divided into three groups. One group was designated as "Mild", consisting of 13 patients having damage up to ⅓ of the nail. One group was designated as "Moderate", consisting of 46 patients having damage from ⅓ to ⅔ of the nail. The final group was designated as "Severe", and consisted of 95 patients having damage from ⅔ to the entire nail.

Final cultures were taken when the nails were 100% recovered from fungal damage clinically or following one year after initial treatment, whichever occurred first.

The conclusions were as follows, of the 13 patients in the Mild category, the cure rate was 100%. Of the 46 patients in the Moderate category, the cure rate was 65%. Of the 95 patients in the Severe category, the cure rate was 36%.

Overall, the combined cure rate for all 154 patients was 49%.

Observations from the clinical trials found that it takes generally 2-4 months to clear a mild condition, 6-12 months for a moderate condition and 9-12+ months for a severe condition with proper medical attention.

Discussion and Conclusions

1. Overall, 49% of the patients treated obtained a clinical cure rate indicating that the topical treatment is more effective than the use of oral terbinafine where terbinafine is only reported as being 25% effective published in the Journal of the American Academy of Dermatology October 2005. Clinical cure rate is defined as physical clear of the nail as well as negative fungal cultures being present.

2. Cost in California of 90 tablets of terbinafine January 2006 was $971.66. 84 tablets of itraconazole sold for $797.71. Six ml of ciclopirox lacquer cost $147.00 (a lacquer is analogous to a coating or paint and is not bound to keratin like cyanoacrylate).

3. Cyanoacrylates have been safely used in medicine for years in wounds, ENT, ophthalmology and cardiac surgery.

4. Cyanoacrylate glues used in securing artificial nails deteriorate over time and water permeated between the natural and artificial nail allowing fungus to attack the natural nail.

5. A composition comprising cyanoacrylate with an antifungal agent (in low concentration) combined with periodic debridement provides a less expensive, effective, safe non oral alternative for the treatment of nail fungus. Synergistic action allows using a lower concentration of antifungal agent, yet has better effect than use of one or the other separately.

6. For best results, patients are recommended to consult with a medical professional for initial treatment and then preferably once per month thereafter.

Conclusion

A less expensive, safe, topical treatment yet more effective than oral therapy for onychomycosis is provided that benefits:

1. Patients unable to tolerate oral medication for health or financial reasons and
2. Those seeking a more effective topical alternative.
3. Onychomycosis can be treated with an effective amount of cyanoacrylate or in combination with an anti-fungal agent such as undecylenic acid or other appropriate agents.
4. The combination of an effective amount of cyanoacrylate and anti-fungal agent further helps to bleach yellow imperfect nails.
5. Dermatophytes need: A) air; B) food=keratin; and, C) water.
6. Cyanoacrylate binds to keratin of nails blocking these essential needs.

Dramatic clinical and cosmetic improvement was evident within weeks after the first debridement and application procedure of the cyanoacrylate/antifungal agent composition.

Summary

Clinical—patients pleased early in course
Culture—comparable to better than oral antifungals
Conclusions—safe, effective, inexpensive
Significant, cost savings Benefits—no drug interactions, no adverse side effects
Cost and Outcome Comparisons

| New topical strategy | Conventional |
| --- | --- |
| 1. Initial office visit & Treatment (Debridement, Application of ECA (cost of topical) | 1. Initial visit and labs |
| | 2. Rx of $1000 or +/− less |
| | 3. Follow up labs |
| | 4. Debridement may be needed |
| 2. Follow up visit with Debridement (topical) | 5. Cure rates of 40-70% and only 25% complete cure of all nails after 1 yr (Warshaw et al. JAAD October 2005) |
| 3. Follow up and reapplication of same again. Then patient can continue home treatments for 6-12 mo or longer if chronic disease | |
| 4. Mycological cure 40-70% with complete cure of all nails after 1 year possible and easily maintained. | |

It is to be realized that only preferred embodiments of the invention have been described and that numerous substitutions, modifications and alterations are permissible without departing from the spirit and scope of this disclosure as defined in the following claims.

The invention claimed is:

1. A method for treating a nail infected with onychomycosis comprising the steps of:
    (a) providing a liquid composition containing alkyl cyanoacrylate;
    (b) performing debridement of the top surface of the infected nail to expose areas adjacent to and below the top surface infected with onychomycosis;
    (c) applying said liquid composition to cover said exposed areas after debridement, said applied liquid composition will subsequently harden to form a hard layer and form a barrier substantially preventing moisture and air contact with the areas of the nail beneath said hard layer still infected with onychomycosis;
    (d) waiting at least three days, then repeating steps (b) and (c); and,
    (e) repeating step (d) until the originally infected nail is substantially cured of onychomycosis.

2. The method of claim 1 where said liquid composition further comprises an antifungal agent that is soluble in said liquid composition and where said composition is synergistically more effective in treating onychomycosis than if the antifungal agent or cyanoacrylate were used separately.

3. The method of claim 1 where said liquid composition comprises alkyl cyanoacrylate in a weight percent range of between 70-95 percent.

4. The method of claim 3 which further comprises an anti fungal agent in a weight percent range of between 0.1 percent and 10 percent.

5. The method of claim 4 which further comprises a stabilizer for affecting the cure rate between 100-2000 parts per million.

* * * * *